(12) United States Patent
Kaizik et al.

(10) Patent No.: US 7,342,144 B2
(45) Date of Patent: Mar. 11, 2008

(54) METHOD FOR PRODUCING 1-OLEFINS BY CATALYTICALLY SPLITTING 1-ALKOXYALKANES

(75) Inventors: Alfred Kaizik, Marl (DE); Dietrich Maschmeyer, Recklinghausen (DE); Dirk Roettger, Recklinghausen (DE); Franz Nierlich, Marl (DE); Cornelia Borgmann, Recklinghausen (DE)

(73) Assignee: OXENO Olefinchemie GmbH, Marl (DE)

( * ) Notice: Subject to any disclaimer, the term of this patent is extended or adjusted under 35 U.S.C. 154(b) by 367 days.

(21) Appl. No.: 10/538,475

(22) PCT Filed: Oct. 28, 2003

(86) PCT No.: PCT/EP03/11919

§ 371 (c)(1),
(2), (4) Date: Jun. 7, 2005

(87) PCT Pub. No.: WO2004/052809

PCT Pub. Date: Jun. 24, 2004

(65) Prior Publication Data

US 2006/0036121 A1    Feb. 16, 2006

(30) Foreign Application Priority Data

Dec. 10, 2002  (DE) .............................. 102 57 499

(51) Int. Cl.
  *C07C 1/00*  (2006.01)
(52) U.S. Cl. ........................ 585/640; 585/638; 585/639
(58) Field of Classification Search ......... 585/638–640
  See application file for complete search history.

(56) References Cited

U.S. PATENT DOCUMENTS

| | | |
|---|---|---|
| 4,395,580 A | 7/1983 | Juguin et al. |
| 6,015,928 A | 1/2000 | Gubisch et al. |
| 6,184,424 B1 | 2/2001 | Bueschken et al. |
| 6,239,318 B1 | 5/2001 | Schuler et al. |
| 6,331,657 B1 | 12/2001 | Kaizik et al. |
| 6,403,836 B2 | 6/2002 | Kaizik et al. |
| 6,407,295 B1 | 6/2002 | Kaizik et al. |
| 6,433,230 B1 | 8/2002 | Bueschken et al. |
| 6,482,992 B2 | 11/2002 | Scholz et al. |
| 6,492,564 B1 | 12/2002 | Wiese et al. |
| 6,500,991 B2 | 12/2002 | Wiese et al. |
| 6,555,716 B2 | 4/2003 | Protzmann et al. |
| 6,570,033 B2 | 5/2003 | Rottger et al. |
| 6,603,047 B2 | 8/2003 | Wiese et al. |
| 6,627,782 B2 | 9/2003 | Kaizik et al. |
| 6,680,414 B2 | 1/2004 | Knoop et al. |
| 6,720,457 B2 | 4/2004 | Drees et al. |
| 6,818,770 B2 | 11/2004 | Selent et al. |
| 6,924,389 B2 | 8/2005 | Jackstell et al. |
| 6,956,133 B2 | 10/2005 | Jackstell et al. |
| 6,960,699 B2 | 11/2005 | Totsch et al. |
| 7,009,068 B2 | 3/2006 | Schmutzler et al. |
| 7,109,346 B2 | 9/2006 | Beller et al. |
| 2004/0059170 A1 | 3/2004 | Rottger et al. |
| 2004/0097773 A1 | 5/2004 | Beckmann et al. |
| 2004/0236133 A1 | 11/2004 | Selent et al. |
| 2004/0238787 A1 | 12/2004 | Wiese et al. |
| 2004/0242947 A1 | 12/2004 | Beller et al. |
| 2004/0260113 A1 | 12/2004 | Bueschken et al. |
| 2005/0038273 A1 | 2/2005 | Rottger et al. |
| 2005/0038285 A1 | 2/2005 | Maschmeyer et al. |
| 2005/0043279 A1 | 2/2005 | Selent et al. |
| 2005/0065387 A1 | 3/2005 | Beller et al. |
| 2005/0101800 A1 | 5/2005 | Büschken et al. |
| 2005/0182277 A1 | 8/2005 | Totsch et al. |
| 2005/0209489 A1 | 9/2005 | Moller et al. |
| 2005/0234270 A1 | 10/2005 | Kaizik et al. |
| 2005/0256281 A1 | 11/2005 | Grund et al. |
| 2006/0041167 A1 | 2/2006 | Grass et al. |
| 2006/0128998 A1 | 6/2006 | Lueken et al. |
| 2006/0129004 A1 | 6/2006 | Lueken et al. |
| 2006/0161017 A1 | 7/2006 | Grass et al. |
| 2006/0241324 A1 | 10/2006 | Moeller et al. |

FOREIGN PATENT DOCUMENTS

| | | |
|---|---|---|
| DE | 101 05 751 | 8/2002 |
| GB | 673 547 | 6/1952 |
| GB | 2 128 972 | 5/1984 |
| WO | WO 92/10450 | * 6/1992 |

OTHER PUBLICATIONS

U.S. Appl. No. 10/538,359, filed Jun. 13, 2005, Rottger, et al.
U.S. Appl. No. 10/517,620, filed Dec. 23, 2004, Rottger, et al.
U.S. Appl. No. 10/562,454, filed Dec. 27, 2005, Krissmann, et al.
U.S. Appl. No. 10/576,302, filed Apr. 19, 2006, Kaizik, et al.
U.S. Appl. No. 10/511,595, filed Nov. 2, 2004, Grass et al.
U.S. Appl. No. 10/579,471, filed May 15, 2006, Zanthoff, et al.
U.S. Appl. No. 11/494,741, filed Jul. 28, 2006, Kaizik, et al.
U.S. Appl. No. 10/588,762, filed Aug. 8, 2006, Wiese, et al.
U.S. Appl. No. 10/584,492, filed Jun. 22, 2006, Ortmann, et al.
U.S. Appl. No. 10/584,148, filed Jun. 22, 2006, Ortmann et al.
U.S. Appl. No. 11/574,063, filed Feb. 22, 2007, Nierlich, et al.

* cited by examiner

*Primary Examiner*—Glenn A. Caldarola
*Assistant Examiner*—In Suk Bullock
(74) *Attorney, Agent, or Firm*—Oblon, Spivak, McClelland, Maier & Neustadt, P.C.

(57) ABSTRACT

The present invention relates to a process for preparing 1-olefins from 1-alkoxyalkanes, in particular to the preparation of 1-octene from 1-alkoxyoctane, by base-catalyzed alcohol cleavage.

8 Claims, No Drawings

METHOD FOR PRODUCING 1-OLEFINS BY CATALYTICALLY SPLITTING 1-ALKOXYALKANES

The present invention relates to a process for preparing 1-olefins from 1-alkoxyalkanes, in particular to the preparation of 1-octene from 1-alkoxyoctane, by catalytic alcohol elimination under nonisomerizing conditions.

Owing to their reactivity, olefins are one of the most important synthetic units in organic chemistry. They are precursors for a multitude of compounds, for example aldehydes, ketones, alcohols, carboxylic acids and halogen compounds. They are used in large amounts to prepare homo- or cooligomers and homo- and copolymers, for example polyethylene or polypropylene.

Ethene and propene are prepared in large amounts worldwide by steamcracking or by catalytic cleavage of hydrocarbons. In these processes, considerable amounts of $C_4$ olefins (isobutene, 1-butene, 2-butenes) and $C_5$ olefins are obtained.

Olefins having more than four carbon atoms have a rapidly increasing number of isomers. A separation of such isomer mixtures, as obtained, for example, in cracking processes, is industrially costly and inconvenient.

Higher olefins may be linear or branched, in which case the position of the double bond may be terminal ($\alpha$-olefins, 1-olefins) or internal. The linear $\alpha$-olefins (LAOs) are the industrially most important product group.

Straight-chain $\alpha$-olefins such as 1-hexene and 1-octene are used in large amounts in the production of various chemical products. For example, surfactants, plasticizers, lubricants and polymers are prepared from 1-octene. An economically important field of use is the use of 1-octene as a comonomer in polymers, especially in modified polyethylene and modified polypropylene.

Higher linear olefins are obtained, for example, by addition polymerization reactions based on ethene or by dehydrochlorination of n-chloroparaffins.

Ethene can be oligomerized with the aid of Ziegler catalysts (triethylaluminum), in which case a mixture of unbranched $\alpha$-olefins having even carbon number is obtained.

Further preparation processes for $\alpha$-olefins are likewise based on ethene as a feedstock, but differ substantially by the catalyst used for the oligomerization (see: "Applied Homogeneous Catalysis with Organometallic Compounds", Edited by B. Cornils, W. A. Herrmann, VCH Verlag Weinheim 1996, Vol. 1, p. 245-258). For instance, a nickel-phosphine complex catalyst is used for the ethene oligomerization in the SHOP process (Shell higher olefin process) developed by Shell (see: K. Weissermel, H.-J. Arpe, "Industrielle Organische Chemie", VCH Verlag Weinheim 1994, 4th ed., p. 95 ff.).

In one variant of the SHOP process, unbranched $\alpha$-olefins having even and odd carbon number can be prepared from ethene. This process comprises three reaction steps, specifically ethene oligomerization, double bond isomerization, i.e. shifting of the double bonds, and cross-metathesis (ethenolysis) of the olefin mixture having internal double bonds with ethene.

For the preparation of olefins based on n-paraffins, useful processes have been found to include thermal cracking, catalytic dehydrogenation and chlorinating dehydrogenation (chlorination and subsequent hydrogen chloride elimination).

In these processes, olefins having predominantly internal double bonds are formed and can be converted to $\alpha$-olefins by cross-metathesis.

However, the abovementioned processes for preparing higher olefins have the disadvantage that a multitude of $\alpha$-olefins of different chain length is always formed, which firstly has to be separated in a costly and inconvenient manner and secondly greatly reduces the yield of the desired $\alpha$-olefin.

The processes employed at present for the preparation of 1-octene are based mainly on the raw material ethene. Olefin mixtures are obtained from which 1-octene is recovered by distillation. For example, it is possible in the SHOP process under optimized reaction conditions to obtain only an olefin mixture having a maximum 1-octene content of 25% by weight.

In addition to the ethene-based processes, the isolation of 1-octene from the product spectrum of the Fischer-Tropsch synthesis has additionally gained industrial significance.

In addition to the ethene-based preparation processes, the literature also discloses processes which use 1,3-butadiene as the raw material for the 1-octene preparation.

When 1,3-butadiene is used as the raw material basis, 1-octene is not obtained by the direct synthetic route, for example via a dimerization, but rather via several reactions steps. For instance, WO 92/10450 describes a process in which 1,3-butadiene is reacted preferentially with methanol or ethanol to give a 2,7-octadienyl ether which, after hydrogenation to the octyl ether (e.g. 1-methoxyoctane), is cleaved over an acidic $\gamma$-$Al_2O_3$ to give 1-octene. EP 0 440 995 follows a similar route, but the reaction is effected in the first step with a carboxylic acid. A characteristic of all processes is the first process step which is referred to generally as telomerization. In the telomerization, a telogen (for example water, methanol, ethanol and carboxylic acid) is generally reacted with a taxogen (1,3-butadiene, 2 equivalents) to give a telomer.

In the known processes for preparing 1-octene based on butadiene, as described, for example in WO 92/10450 or EP 0 440 995, the 1-octene is obtained by cleavage of a 1-substituted n-octane (alkoxyoctane). The selectivities in this step are often unsatisfactory. For instance, in WO 92/10450, a selectivity for octenes of only 66% is achieved at a conversion of 80% in the cleavage of 1-methoxyoctane over pure alumina or over acid-modified alumina.

The cleavage of 1- and 2-octanols and $C_8$-alkyl esters, and of 1-alkoxyoctane to 1-octene, is also known in the patent literature.

The cleavage of tert-butanol to water and isobutene is carried out in EP 0 726 241 by means of acidic ion exchangers in a reactive distillation. The application of this reactor design to the cleavage of methyl tert-butyl ether to water and isobutene can be taken from EP 1 149 814.

JP 02172924 describes the cleavage (dehydration) of 1-octanol, which has been obtained by a telomerization reaction of 1,3-butadiene with water and subsequent hydrogenation, to 1-octene and water. One catalyst used for the cleavage is a sodium hydroxide-modified calcium phosphate.

EP 0 440 995 describes the thermal cleavage of alkyl esters, obtained from a telomerization reaction and subsequent hydrogenation, to 1-octene. No catalysts are used in the cleavage reaction.

The cleavage of alkoxyalkanes (ethers) to olefins is likewise known. Some studies were published at the start of the 20th century, for example the cleavage of ethers over Japanese acid clay (W. Ipatiew, Berichte der Deutschen Chemischen Gesellschaft, 1904, 37, 2961; K. Kashima, Bull. Chem. Soc. Jpn. 1930, 25).

The cleavage of a methyl ether in the presence of alumina, aluminum phosphates, aluminum silicates and mixtures of aluminum silicates with metal phosphates and metal sulfates is the subject matter of the patent U.S. Pat. No. 2,561,483.

CN 1158277 A claims catalysts selected from modified silicon oxide ($SiO_2$), thorium oxide ($ThO_2$), the oxides of the alkaline earth metals, of the rare earths and of the metals of group IV B for the cleavage of alkoxyalkanes (ethers).

CN 1165053 discloses the cleavage of 1-methoxyoctane (octyl methyl ether) to 1-octene in the presence of a magnesium oxide-modified silicon oxide. It was possible using these $MgO$—$SiO_2$ catalysts to achieve 1-octene selectivities of over 95% at 1-methoxyoctane conversions of over 80%.

The cleavage of 1-alkoxyalkanes can be carried out either in the liquid phase or in the gas phase. In general, the cleavage of 1-alkoxyalkanes to 1-olefins is carried out as a heterogeneously catalyzed gas phase reaction. For this purpose, DE 101 05 751 discloses the use of $SiO_2$ and $Al_2O_3$, both unmodified as a pure substance.

In summary, it can be stated that the known processes for cleaving alkoxyalkanes or alkanols are carried out over acidic catalysts such as sulfonated ion exchange resins, $Al_2O_3$ or $SiO_2$. However, acidic compounds catalyze not only the cleavage but also the isomerization of the resulting 1-olefins to olefins having internal double bonds.

In addition to the desired 1-olefin product of value, the by-products formed are undesired internal olefins which can be removed from the 1-olefin product of value only with difficulty. Under isomerizing conditions, a 1-olefin can be converted to olefins having internal double bonds until the thermodynamic equilibrium is established. In the preparation of 1-olefins, the formation of olefins having internal double bonds (internal olefin isomers) is undesired for two reasons, firstly owing to the yield loss and secondly owing to the level of technical complexity for the removal of the 1-olefin from internal olefin isomers, since the boiling points of the isomeric olefins are close to one another.

The requirement for an industrial process for preparing a 1-olefin from a 1-alkoxyalkane or from an alkanol is therefore a selective cleavage to the target product, with substantial minimization of a subsequent isomerization of the 1-olefin formed.

It has now been found that the selectivity of the cleavage of methoxyalkanes to 1-olefins and the ratio of 1-olefin to internal olefins is distinctly improved in the presence of basic catalysts based on modified aluminas or zirconia in comparison to the acidic catalysts used to date.

The invention provides a process for preparing α-olefins having from 3 to 16 carbon atoms by catalytically cleaving 1-alkoxyalkanes, wherein the cleavage is carried out over alumina and/or zirconia containing from 0.01 to 10% by weight of at least one alkali metal and/or alkaline earth metal oxide.

In the process according to the invention, alkoxyalkanes having the general structure (R1)-$CH_2$—$CH_2$—O(R2) can be converted over the inventive catalysts to the corresponding 1-olefins having the general structure (R1)-CH=$CH_2$.

Analogously, compounds of the general formulae (R1)-$CH_2CH_2$—OH or (R1)CH(OH)$CH_3$ can be converted to 1-olefins having the formula (R1)-CH=$CH_2$.

The group (R1) is preferably a hydrocarbon group having from 1 to 14 carbon atoms; the group (R2) is preferably a hydrocarbon group having from 1 to 4 carbon atoms.

Preferred products of the process according to the invention are 1-octene, 1-pentene, isobutene or 1-butene.

The α-olefins prepared by the process according to the invention have preferably from 4 to 8 carbon atoms.

In the cleavage of 1-alkoxyalkanes, 1-methoxyoctane, 1-ethoxyoctane, tert-butyl methyl ether and/or tert-amyl methyl ether, tert-amyl ethyl ether or tert-amyl butyl ether in particular are cleaved to the corresponding α-olefins and alcohols, and the olefin obtained is preferably 1-octene, 1-pentene, isobutene or 2-methyl-1-butene.

In the process according to the invention, the cleavage of the 1-alkoxyalkanes to the 1-olefin is preferably carried out as a heterogeneously catalyzed gas phase reaction.

The catalysts used in the process according to the invention are preferably basic and strongly basic catalysts. The catalysts used in accordance with the invention contain, as main components, alumina and/or zirconia, and also alkali metal and/or alkaline earth metal oxides. As further components, the catalyst may comprise titanium dioxide, silicon dioxide and/or thorium oxide at from 0.01 to 3% by weight, preferably from 0.5 to 5% by weight. These catalysts are basic in the context of the present invention.

The proportion of basic metal oxides (hydroxides are converted to oxides by calculation) in the catalyst is preferably from 0.01 to 10% by mass, more preferably from 0.1 to 5% by mass, especially preferably from 0.1 to 3% by mass. Preferred alkali metal oxides are sodium oxide and/or potassium oxide. The alkaline earth metal oxides used are preferably magnesium oxide, strontium oxide and/or barium oxide.

Preference is given to using γ-aluminas having a BET surface area of from 80 to 350 $m^2$/g, preferably 120-250 $m^2$/g. The catalysts are prepared by known methods. Common methods are, for example, precipitation, impregnation or spraying of an $Al_2O_3$ body with an appropriate salt solution and subsequent calcination.

The catalysts are appropriately used in the form of spheres, tablets, cylinders, extrudates or rings.

The 1-alkoxyalkane can be cleaved in the presence of substances which are inert or substantially inert under the cleavage conditions. For example, nitrogen or argon, but also water, steam or alkanes, for example, methane, propane or else dimethyl ether, may be added. The proportion of these inert substances is preferably between 0 and 90% by volume, more preferably between 0 and 50% by volume and, between 0 and 30% by volume and, between 0 and 20% by volume or between 0 and 10% by volume.

In the process according to the invention, the cleavage of the 1-alkoxyalkanes is carried out continuously or batchwise over suspended catalysts or particulate catalysts arranged in a fixed bed in the gas phase or mixed liquid/gas phase. Preference is given to carrying out the continuous cleavage over catalysts arranged in a fixed bed.

In the continuous cleavage, different process variants may be selected. It may be carried out in one or more stages, and adiabatically, polytropically, preferably virtually isothermally, i.e. with a temperature differential of typically less than 10° C. In the latter case, all reactors, appropriately tubular reactors, can be operated virtually isothermally. Preference is given to operating the cleavage in straight pass. However, it may also be operated with product recycling. It is possible to at least partly remove the products between the reactors.

1-Alkoxyalkanes can be cleaved at temperatures between 100 and 600° C., preferably between 200 and 450° C., more preferably between 280 and 350° C. The cleavage may also be carried out at distinctly lower temperatures, for example 100-250° C., preferably 100-200° C., for example in the cleavage of methyl tert-butyl ether (MTBE) or tert-amyl methyl ether (TAME).

The pressure (absolute) under which the cleavage is carried out is typically between 0.1 and 25 bar. Preference is given to pressures between 0.2 and 10 bar, more preferably between 1 and 5 bar. The weight hourly space velocity (WHSV), reported in grams of reactant per gram of catalyst per hour, is preferably from 0.01 to 30 $h^{-1}$, more preferably 0.1-15 $h^{-1}$, most preferably 0.5-10 $h^{-1}$.

The cleavage of the 1-alkoxyalkanes to 1-olefins may be carried out under full or partial conversion. Unconverted reactant may, after the 1-olefin formed and any other cleavage products have been removed, be recycled into the cleavage. However, it is also possible to only remove the 1-olefin and optionally a portion of the cleavage products and to recycle the remainder into the prepurification before the actual cleavage.

Preference is given to carrying out the cleavage under partial conversion. In this case, the conversion is between 10 and 95%, more preferably between 30 and 95%, most preferably between 70 and 95%.

The target product, the 1-olefin, is removed from the other components of the effluent of the cleavage by known processes, for example phase separation, extraction, scrubbing or distillation.

The reaction effluent is separated into an olefin fraction and a fraction which comprises unconverted alkoxyalkane, alcohol, water and any other by-products. The olefin fraction consists to an extent of more than 85%, preferably more than 90%, in particular from 95 to over 98%, of 1-olefin. Optionally, it is worked up to give even purer 1-olefin. The unconverted reactant may be recycled into the cleavage reactor.

The 1-olefins prepared by the process according to the invention may be used as comonomers in the preparation of polyolefins. In addition, they may be a starting material for organic syntheses.

The process according to the invention has the following advantages: in the product mixture after the cleavage, the proportion of internal olefins which can only be removed with difficulty, if at all, from the 1-olefin product of value is low. The olefin fraction in the case of the cleavage of 1-methoxyoctane consists to an extent of from 91.5 to 98.5% of 1-octene, from 1 to 8.4% of 2-octene and from 0.1 to 2.0% of 3-, 4-octene isomers, so that economically viable recovery of pure 1-octene is possible.

The catalysts used have a long lifetime in the process, since carbonization, as observed when acidic catalysts such as $SiO_2$ are used, is almost completely absent.

The examples which follow are intended to illustrate the invention without restricting its field of application which is evident from the description and the claims:

EXAMPLES

Example 1

Preparation of a Ba-Modified $Al_2O_3$ Catalyst

For the preparation of the inventive catalyst, an acidic γ-alumina with an $Na_2O$ content <300 ppm from Axens was used. The alumina having a BET surface area of 225 $m^2/g$ and a pore volume of 0.68 ml/g was present in extrudate form (cylinder having a length of 4-6 mm and a diameter of 1.25 mm). The barium precursor used for the basic modification of the alumina with barium oxide (BaO) was barium nitrate $Ba(NO_3)_2$.

Before the application of the barium salt, the alumina was first dried in a forced-air drying cabinet at 90° C. for 5 hours. The dried extrudates were subsequently impregnated in a rotating drum (coating drum) at room temperature with the barium nitrate solution using a spray nozzle. The desired barium content in the extrudates to be impregnated may be varied via the concentration of the Ba salt solution. After the impregnation, the $Al_2O_3$ extrudates laden with the barium salt were first dried in a forced-air drying cabinet at 110° C. for 5 hours. The subsequent calcination in which the barium salt is converted to barium oxide or a barium/aluminum/oxygen compound was effected in a fluidized bed reactor in an air stream at 450° C. for 10 hours.

Example 2

Preparation of an Na-Modified $Al_2O_3$ Catalyst

For the preparation of the Na-modified $Al_2O_3$ catalyst, the acidic γ-alumina with $Na_2O$ content <300 ppm from Axens which was described in Example 1 was used.

The impregnating solution used was an aqueous sodium hydroxide solution.

The application of the sodium hydroxide solution to the $Al_2O_3$ extrudates and the thermal aftertreatment (drying and calcination) of the catalyst were carried out by the preparation method described in Example 1.

Example 3

(Comparative Example) Cleavage of 1-Methoxyoctane Over an Unmodified γ-$Al_2O_3$ Catalyst 1-Methoxyoctane (1-MOAN, methyl n-octyl ether), obtained by hydrogenating 1-methoxyoctadiene (telomerization product of 1,3-butadiene with methanol), was used with a purity of about 98% by weight (2% high boilers) for the cleavage in an electrically heated fixed bed flow reactor in the presence of a catalyst. The catalyst (Cat. 1) is a commercial, high-surface area, acidic γ-$Al_2O_3$ (BET surface area 225 $m^2/g$, pore volume 0.68 $cm^3/g$) with the name Spheralite 521C from Axens.

Before entry into the reactor, the liquid reactant was evaporated at 220° C. in an upstream evaporator. At a reaction temperature of 300° C. and a pressure of 1 bar in the reactor, 75.0 g/h of reactant per hour were passed through 13.9 g of catalyst in extrudate form in the gas phase, corresponding to a WHSV value of 5.4 $h^{-1}$. The gaseous product was cooled in a condenser and collected in liquid form in a glass receiver.

The GC analysis of the cleavage product is reproduced in Table 1, column 2.

According to the present results, the following octene selectivities were achieved at a 1-MOAN conversion of about 84.6%: 1-octene product of value sel. 86.7%; by-products: internal $C_8$ isomers: 2-octenes sel. 5.7% and 3-/4-octenes sel. 2.1%

TABLE 1

Cleavage of 1-methoxyoctane over unmodified γ-Al$_2$O$_3$ catalyst

| Component | Example 3 Cat. 1 (comparison) | Example 4 Cat. 2 (invention) | Example 5 Cat. 3 (invention) |
|---|---|---|---|
| 1-Octene | 56.59 | 59.39 | 60.41 |
| t-4-Octene | 0.38 | 0.01 | 0.01 |
| 3-Octenes/c-4-octene | 0.96 | 0.44 | 0.33 |
| t-2-Octene | 0.96 | 0.99 | 0.73 |
| c-2-Octene | 2.75 | 2.97 | 1.75 |
| Methanol | 2.45 | 2.48 | 2.90 |
| Dimethyl ether | 11.26 | 10.89 | 10.84 |
| Water | 4.40 | 4.26 | 4.24 |
| 1-MOAN | 16.38 | 15.84 | 13.16 |
| Remainder | 3.88 | 2.74 | 5.71 |

Example 4

(According to the Invention) Cleavage Over Ba-Modified γ-Al$_2$O$_3$ Catalyst

The product of the hydrogenation of 1-methoxyoctadiene, the 1-methoxyoctane (1-MOAN), was used with a purity of about 98% by weight (2% high boilers) for the cleavage in a fixed bed flow reactor, as described in Example 3, in the presence of a BaO-modified alumina (Al$_2$O$_3$ with 1.0% by weight of BaO) from Example 1.

At a reaction temperature of 300° C. and a pressure of 1 bar in the reactor, 50 g of methoxyoctane per hour were passed through 14.1 g of catalyst in cylinder form in the gas phase, corresponding to a WHSV value of 3.5 h$^{-1}$. As in Example 3, the gaseous product was cooled in a condenser and collected in liquid form in a glass receiver.

The GC analysis of the cleavage product is reproduced in Table 1, column 3 (Cat. 2.).

As can be taken from Table 1, the 1-MOAN is cleaved distinctly more selectively to the 1-octene product of value with lower formation of 3- and 4-octene isomers over Ba-modified alumina in comparison to unmodified, acidic γ-alumina (Cat. 1) at complete MOAN conversions.

At a 1-MOAN conversion of about 83.7%, the following octene selectivities were achieved over the inventive catalyst: 1-octene product of value sel. 94.2%; by-products: internal C$_8$ isomers: 2-octenes sel. 5.0% and 3-/4-octenes sel. 0.7%.

Example 5

(According to the Invention) Cleavage Over Na-Modified γ-Al$_2$O$_3$ Catalyst

As in Examples 3 and 4, the product of the hydrogenation of 1-methoxyoctadiene, the 1-methoxyoctane (1-MOAN, methyl n-octyl ether), was used as the reactant for the gas phase cleavage in a fixed bed flow reactor. The catalyst used was an alumina modified with sodium hydroxide solution (Al$_2$O$_3$ with 1.5% by weight of Na$_2$O) from Example 2.

At a reaction temperature of 350° C. in the reactor, 25 g per hour of methoxyoctane were passed through 13.5 g of catalyst in extrudate form in the gas phase, corresponding to a WHSV value of 1.8 h$^{-1}$. The gaseous product was cooled in a condenser and collected in liquid form in a glass receiver.

The GC analysis of the cleavage product is reproduced in Table 1, column 4.

As can be taken from Table 1, the 1-MOAN is also cleaved with a high 1-octene selectivity to the desired 1-octene product of value over an Na-modified γ-alumina (Cat. 3) with low formation of 3-, 4-octenes.

At a 1-MOAN conversion of about 86.2%, the following octene selectivities were achieved: 1-octene product of value sel. 93.8%; by-products: internal C$_8$ isomers: 2-octenes sel. 3.9% and 3-/4-octenes sel. 0.5%.

The by-products listed under remainder include components which can likewise be cleaved to 1-octene, including dioctyl ether. These too may optionally be recycled into the cleavage.

Example 6

(According to the Invention) Cleavage of Methyl Tert-Butyl Ether (MTBE) Over an Na-Modified γ-Al$_2$O$_3$ Methyl tert-butyl ether (MTBE, tert-butyl methyl ether) from Oxeno having a purity of 99.94% by weight was used as the reactant for the catalytic gas phase cleavage in a fixed bed flow reactor. The catalyst used for the cleavage was a γ-alumina modified with sodium hydroxide solution (Al$_2$O$_3$ with 1.5% by weight of Na$_2$O) from Example 2.

Before entry into the reactor, the liquid reactant was evaporated at 180° C. in an upstream evaporator. At a reaction temperature of 235° C. and a pressure of 1 bar, 15 g per hour of methyl tert-butyl ether were passed through 20.0 g of catalyst in extrudate form in the gas phase, corresponding to a WHSV. value of 0.75 h$^{-1}$. The gaseous reaction effluent was cooled in a condenser and collected in liquid form in a glass receiver.

According to the GC analysis, the reaction effluent contains, in addition to the unconverted methyl tert-butyl ether reactant (38.0% by weight of MTBE), the following cleavage products: 38.83% by weight of isobutene, 21.58% by weight of methanol, 1.06% by weight of dimethyl ether, 0.43% by weight of water and 0.10% by weight of 2,4,4-trimethylpentenes.

According to this result, very high selectivities (>99.7%) for the isobutene target product are achieved at MTBE conversions of about 62%. The selectivities of the MTBE cleavage for methanol are, as a result of the dimethyl ether formation, about 95.5%.

What is claimed is:

1. A process for preparing α-olefins having from 3 to 16 carbon atoms by catalytically cleaving 1-alkoxyalkanes, wherein the cleavage is carried out over alumina and/or zirconia comprising from 0.01 to 10% by weight of at least one alkali metal oxide and/or alkaline earth metal oxide.

2. The process as claimed in claim 1, wherein the alkali metal oxide is potassium oxide and/or sodium oxide.

3. The process as claimed in claim 1, wherein the alkaline earth metal oxide is strontium oxide, magnesium oxide and/or barium oxide.

4. The process as claimed in claim 1, wherein the catalyst additionally comprises from 0.01 to 5% by weight of titanium oxide, silicon dioxide and/or thorium oxide.

5. The process as claimed in claim 1, wherein the catalytic cleavage is carried out up to a conversion of from 10 to 95%.

6. The process as claimed in claim 1, wherein the cleavage is carried out in the gas phase.

7. The process as claimed in claim 1, wherein the cleavage is carried out at a temperature of from 100 to 600° C.

8. The process as claimed in claim 1, wherein 1-methoxyoctane, 1-ethoxyoctane, tert-butyl methyl ether, tert-amyl methyl ether, tert amyl ethyl ether or tert-amyl butyl ether is cleaved to the corresponding α-olefins and alcohols.

* * * * *